(12) United States Patent
Heacock

(10) Patent No.: US 8,303,116 B2
(45) Date of Patent: Nov. 6, 2012

(54) MOLDED OPHTHALMIC LENS

(76) Inventor: Gregory Lee Heacock, Auburn, WA (US)

( * ) Notice: Subject to any disclaimer, the term of this patent is extended or adjusted under 35 U.S.C. 154(b) by 150 days.

(21) Appl. No.: 12/941,164

(22) Filed: Nov. 8, 2010

(65) Prior Publication Data
US 2012/0113392 A1   May 10, 2012

(51) Int. Cl.
*A61B 3/10* (2006.01)
(52) U.S. Cl. .............................................. 351/219
(58) Field of Classification Search .............. 351/200, 351/219
See application file for complete search history.

(56) References Cited

U.S. PATENT DOCUMENTS

| 3,589,800 | A  | * | 6/1971 | Cardona | 351/221 |
| 2002/0159031 | A1 | * | 10/2002 | Kanngiesser | 351/219 |
| 2003/0147046 | A1 |   | 8/2003 | Shadduck | |

OTHER PUBLICATIONS

Notification of Transmittal of the International Search Report dated Jan. 19, 2012 in International Application No. PCT/US2011/056117; International Search Report and Written Opinion of the International Searching Authority, or the Declaration.

* cited by examiner

*Primary Examiner* — James Greece
(74) *Attorney, Agent, or Firm* — McAndrews, Held & Malloy Ltd.

(57) ABSTRACT

An ophthalmic is injection molded and/or, compression molded to provide a single use lens. The ophthalmic lens has a larger clear aperture than known lenses of the same type to improve the optical quality of the lens.

57 Claims, 3 Drawing Sheets

MOLDED OPHTHALMIC LENS

FIELD OF THE INVENTION

The present invention relates to an ophthalmic lens and more particularly to a molded ophthalmic lens that has improved optical qualities and that can be manufactured in high volumes at low costs.

CROSS-REFERENCE TO RELATED APPLICATIONS

N/A

STATEMENT REGARDING FEDERALLY SPONSORED RESEARCH OR DEVELOPMENT

N/A

BACKGROUND OF THE INVENTION

Ophthalmic lenses are used by ophthalmologists and optometrists for diagnosis and treatment of the eye. Known ophthalmic lenses as shown in FIG. 1 are machined to have a main body portion 10 with a conic shape and at least one mirror surface 12 in the optical path used by the clinician to view or treat the eye. Because known ophthalmic lenses are machined, they are extremely costly to manufacture and cannot be produced in high volumes.

SUMMARY OF THE INVENTION

In accordance with the present invention, the disadvantages of prior ophthalmic lenses have been overcome. The ophthalmic lens of the present invention is a molded lens that has a curved shape and a larger clear aperture than prior ophthalmic lenses of the same type. The ophthalmic lens of the present invention can be mass produced in large volumes with a high optical quality. Further, because the clear aperture of the ophthalmic lens of the present invention is larger than known ophthalmic lenses of the same type, the optical path used by the clinician is larger than the optical path of known ophthalmic lenses. As a result, with the ophthalmic lens of the present invention, the need to manipulate or rotate the lens during examination is reduced thereby reducing the potential for abrasion of the cornea by the ophthalmic lens. The clinician can also more quickly view the interior of the eye for diagnosis and/or treatment. Moreover, because of the larger clear aperture, the clinician may perform procedures not possible with a conventional ophthalmic lens.

More particularly, in accordance with one embodiment, the ophthalmic lens of the present invention includes a grip portion, an eye contacting portion and a main body portion disposed between the grip portion and the eye contacting portion wherein the grip portion, the eye contacting portion and the main body portion are integrally formed of polymethylmethacrylate having a specific gravity of 1.1-1.8 and an index of refraction of 1.2-2.0. The eye contacting portion is shaped to contact the cornea of the eye. The main body portion has a curved sidewall with an arc extending from the grip portion to the eye contacting portion wherein the arc has a length that is at least 1.15 times the length of a chord of the arc. The main body also includes at least one mirror surface for reflecting light to and from the eye contacting portion.

In accordance with another embodiment of the present invention, the ophthalmic lens includes an eye contacting portion and a magnifying portion opposite the eye contacting portion, the eye contacting portion and the magnifying portion being integrally formed of molded polymethylmethacrylate having a specific gravity of 1.1-1.8, the ophthalmic lens having a clear aperture of at least 11.5 mm and a length of at least 9 mm.

In accordance with a further embodiment of the present invention, the ophthalmic lens includes an eye contacting lens and an entry lens, each formed of molded polymethylmethacrylate having a specific gravity equal to or less than 1.19 and an index of refraction of 1.2-2.0. The anterior surface of the eye contacting lens is aspheric. The entry lens is bi-aspheric and has a diameter of 35 mm or less. A holder spaces the entry lens from the eye contacting lens such that the length of the ophthalmic lens from a posterior surface of the eye contacting lens to the anterior surface of the entry lens is 34 mm or less.

In one embodiment of the present invention, the ophthalmic lens is injection molded and/or compression molded.

These and other objects, advantages and novel features of the present invention, as well as details of an illustrated embodiment thereof, will be more fully understood from the following description and the drawing.

DETAILED DESCRIPTION OF THE PREFERRED EMBODIMENT

Figure 1:
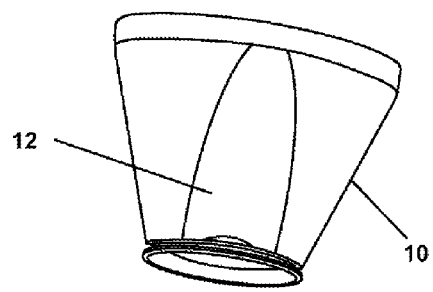
FIG. 1 is a perspective view of a prior art ophthalmic lens.
Figure 2:
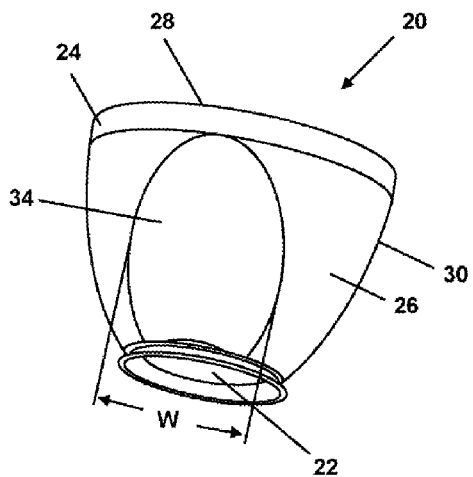
FIG. 2 is a perspective view of a molded ophthalmic lens in accordance with one embodiment of the present invention.

An ophthalmic lens 20 in accordance with one embodiment of the present invention, as shown in FIG. 2, has an eye contacting portion 22, a grip portion 24 and a main body portion 26 disposed between the eye contacting portion 22 and the grip portion 24. The eye contacting portion 22 of the ophthalmic lens 20 is shaped to match a cornea of an eye. In a preferred embodiment, the eye contacting portion of the lens has a diameter of approximately 12.5 mm and a radius curvature of 7.75 mm. The grip portion 24 of the ophthalmic lens 20 may have a generally cylindrical sidewall. In a preferred embodiment, the grip portion 24 is textured so that a clinician can easily maintain his grip on the lens 20 during diagnosis or treatment. It is noted that, if desired, a larger grip surface may be added over the grip portion 24. The surface 28 of the lens 20 opposite of the eye contacting portion 22 may be planar or curved for magnification.

The eye contacting portion 22, the main body portion 26, and the grip portion 24 of the ophthalmic lens 20 are integrally formed of a molded, optical grade, acrylic resin. In a preferred embodiment, the acrylic resin is polymethylmethacrylate. The acrylic resin may have a specific gravity of 1.1-1.8. In a preferred embodiment, the specific gravity of the acrylic resin is 1.15-1.19 and the index of refraction of the acrylic resin is between 1.2 and 2.0. The molded ophthalmic lens may be injection molded and/or, compression molded.

Figure 3:
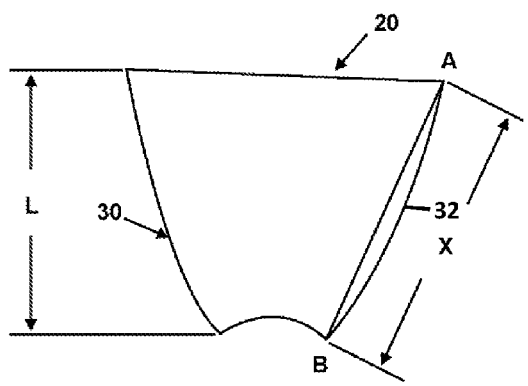
FIG. 3 is an illustration of the arc and chord of the curved main body portion of the ophthalmic lens of FIG. 2.

In order to optimize the ophthalmic lens 20 for molding, the main body portion 26 of the ophthalmic lens 20 has a sidewall 30 that is curved in two dimensions or curved about at least two axes. In a preferred embodiment, the curved sidewall 30 is described by a sphere having a centerline that does not coincide with the center line of the lens 20. As shown in FIGS. 2 and 3, the curved sidewall 30 has an arc 32 that extends from the grip portion 24 at point A to the eye contacting portion 22 at point B. The length of the arc 32 is equal to or greater than 1.15 times the length X of the chord AB, i.e. the line segment extending from point A to point B. The shape of the sidewall 30 having an arc 32 that extends in a direction from the grip portion 24 towards the eye contacting portion 22 allows any debris, bubbles and the like that tend to adhere to the surface of the mold during the molding process to collect away from the optical centerline of the lens so as to improve the optical quality of the molded ophthalmic lens. Moreover, the shape of the curved sidewall with the arc 32 also minimizes shrinkage during the molding process.

The main body 26 of the ophthalmic lens 20 is also molded with at least one flat mirror surface 34. An additional benefit of the curved shape of the main body 26 is that the mirror surface(s) of the ophthalmic lens 20 are larger than those of prior ophthalmic lenses of the same type. As such, the optical pathway used by the clinician during examination of the patient's eye is larger thereby reducing the need to manipulate or rotate the ophthalmic lens 20 during the examination. This improves the examination and/or treatment procedure by allowing the clinician to view the interior of the eye more quickly. Moreover, the potential for abrasion of the patient's cornea from lens manipulation is reduced. For an ophthalmic lens 20 having a single mirror surface 34, the width W of the mirror surface 34 may be at least 13 mm and preferably 13.7 mm or greater. The length, L, of the ophthalmic lens 20 is at least 21 mm. In a preferred embodiment the mirror surface 34 has an aluminum coating.

Figure 4A:
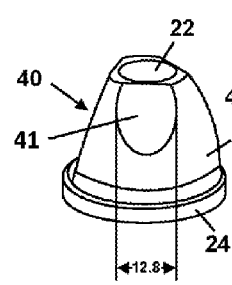
FIG. 4A is a perspective view of an ophthalmic lens in accordance with the present invention having three mirrors with the first or Gonio mirror being shown.
Figure 4B:
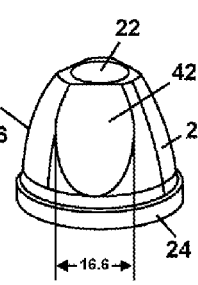
FIG. 4B is a perspective of the ophthalmic lens having three mirrors of FIG. 4A with the second or periphery mirror being shown.
Figure 4C:
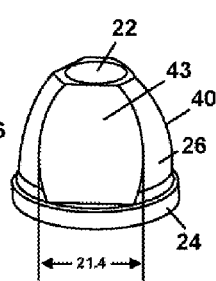
FIG. 4C is a perspective view of the ophthalmic lens having three mirrors of 4A with the third or Arcades mirror being shown.
Figure 6:
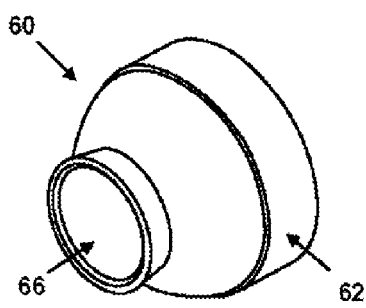
FIG. 6 is a perspective view of another embodiment of the ophthalmic lens of the present invention.

FIGS. 4A-4C illustrates an ophthalmic lens 40 having three mirror surfaces 41, 42 and 43 formed in the curved main body portion 26 of the lens 40. The length L of the ophthalmic lens 40 is at least 27.5 mm. The first mirror surface 41 may be a Gonio mirror having a width that is at least 12 mm and preferably 12.8 mm or greater. The second mirror surface 42 of the ophthalmic lens 40 may be a periphery mirror having a width that is at least 15.6 mm and preferably 16.6 mm or greater. The third mirror surface 43 of the lens 40 may be an Arcades mirror having a width of at least 20 mm and preferably 21.4 mm or greater. In a preferred embodiment, each of the mirror surfaces 41, 42 and 43 has an aluminum coating.

Figure 5:
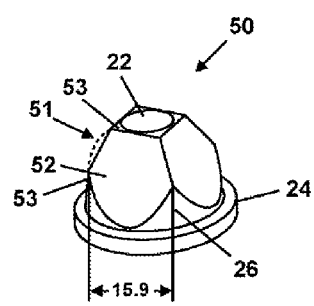
FIG. 5 is a perspective view of a Gonio lens in accordance with the present invention.

FIG. 5 illustrates a Gonio lens 50 having four flat mirror surfaces 52 formed in the curved main body portion body 26 of the ophthalmic lens 50. The length, L of the lens 50 is at least 17 mm. It is noted that because the flat mirror surfaces 52 of the Gonio lens 50 are contiguous, a portion 51 of the arc 32 is projected as shown by the dotted line. As such, the arc 32 of the Gonio lens includes real portions 53 on opposite sides of the projected portion 51 wherein the length of the arc 32, i.e. the sum of the lengths of the real portions 53 and the projected portion 51, is at least 1.15 times the length of the chord of the arc 32. Each of the mirror surfaces 52 may have a width of at least 15.5 mm and preferably 15.9 mm or greater. In a preferred embodiment, each of the mirror surfaces 52 has an aluminum coating.

Figure 7:
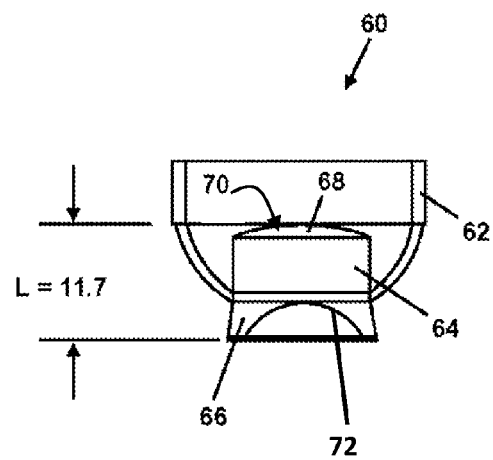
FIG. 7 is a cross sectional view of the lens of FIG. 6 for a capsulotomy lens.
Figure 8:
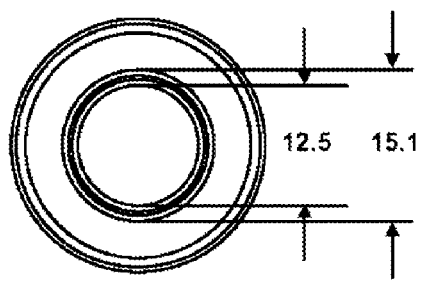
FIG. 8 is a top view of the lens of FIG. 6.
Figure 9:
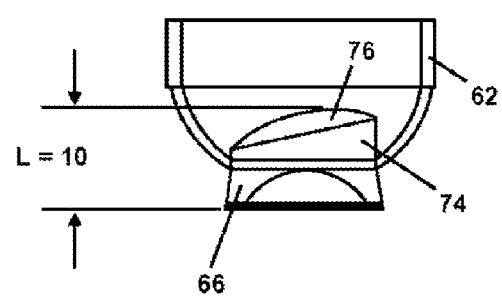
FIG. 9 is a cross sectional view of the lens of FIG. 6 for a iridotomy lens.

In another embodiment of the ophthalmic lens 60 of the present invention, as depicted in FIGS. 6-9, the lens 60 includes a non-integral holder 62 that is made separately from the optical lens 64. The optical or ophthalmic lens 64 includes an eye contacting portion 66 and a magnifying portion 68 that are integrally formed of polymethylmethacrylate having a specific gravity of 1.1-1.8 and preferably 1.15-1.19. The index of refraction of the ophthalmic lens 64 is 1.2-2.0 and preferably 1.49. The ophthalmic lens 64 is injection molded and/or compression molded. The ophthalmic lens 64 has a clear aperture of at least 11.5 mm and preferably at least 12.5 mm. The clear aperture is the diameter of the most anterior surface 70 of the ophthalmic lens 64 into which a clinician looks. The most posterior surface of the ophthalmic lens 64 is the surface 72 contacting the patient's eye. It is noted that in the embodiments of FIGS. 2-6, the clear aperture of an ophthalmic lens having a mirror in the optical path is the width of the mirror. For a capsulotomy lens as shown in FIG. 7, the length of the ophthalmic lens 64 is at least 9 mm and preferably 11.7 mm. For an iridotomy lens 74 as shown in FIG. 9, the length of the ophthalmic lens 74 is at least 9 mm and preferably at 10 mm and the clear aperture is at least 11.5 mm and preferably 12.5 mm. The iridotomy lens 74 is the same as the capsulotomy lens 64 having an eye contacting portion 66 and a magnifying portion 76 integrally formed of polymethylmethacrylate as described above except that the magnifying portion 76 is de-centered. That is, the vertex of the magnifier of the iridotomy lens is off-center from the optical center line of the eye contacting portion 66. It is noted that a clear aperture of 11.5 mm and preferably 12.5 mm is larger than the clear aperture of prior capsulotomy and iridotomy lenses. This is extremely advantageous. For example, the larger aperture allows a physician to perform a peripheral capsulotomy which could not be performed with prior known capsulotomy lenses.

Figure 10:
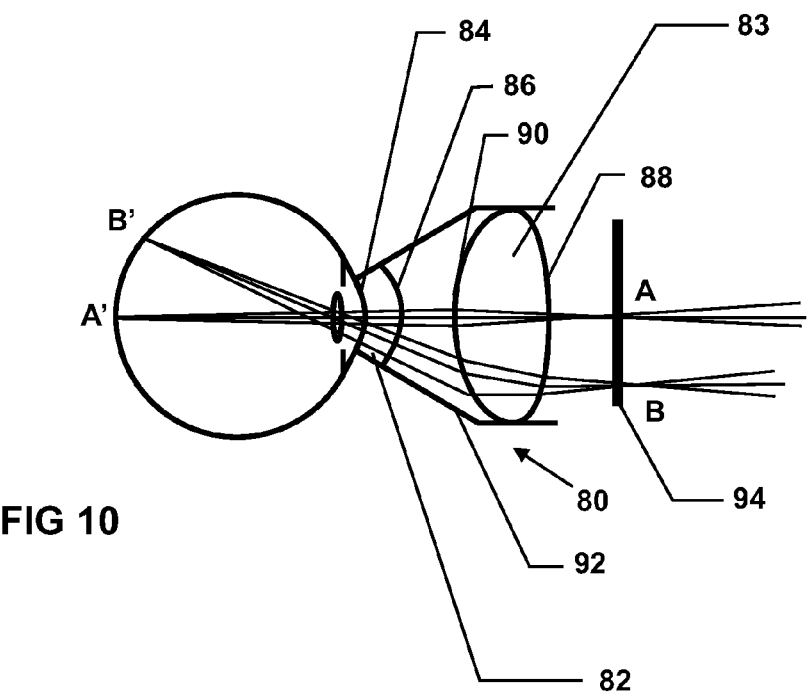
FIGS. 10 and 11 are illustrations of a further embodiment of the ophthalmic lens of the present invention for an indirect lens that is used for observing the fundus of an eye.
Figure 11:
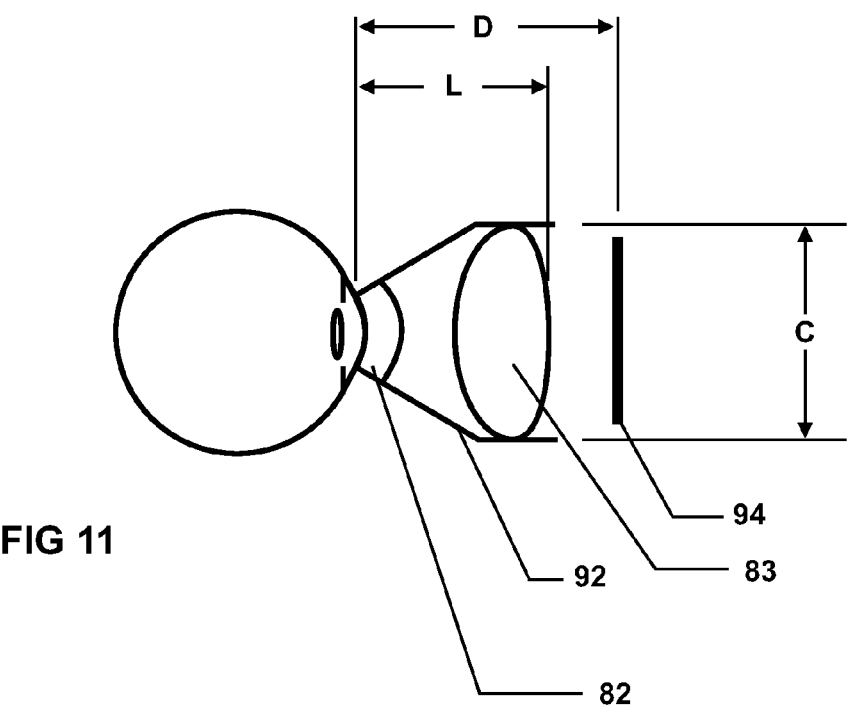

In a further embodiment of the present invention, an indirect ophthalmic lens 80 for observing the fundus of an eye, as shown in FIG. 10, includes an eye contacting lens 82 and an entry lens 83 supported by a holder 92. Each of the eye contacting lens 82 and the entry lens 83 are formed of molded polymethylmethacrylate having a specific gravity of 1.1-1.8 and preferably 1.15-1.19 and an index of refraction of 1.2-2.0 and preferably 1.49. The eye contacting lens 82 and the entry lens 83 are injection molded and/or compression molded. The eye contacting lens 82 has a posterior surface 84 having a radius of curvature that is substantially the same as the surface of a cornea. The anterior surface 86 of the eye contacting lens has an aspheric shape such that the light rays entering the patient's eye through the contact lens 82 are focused unto the fundus of the patient's eye. The entry lens 83 is positioned anterior to the eye contacting lens 82 wherein the optical axes of the eye contacting lens 82 and the entry lens 83 are substantially coincident. Each of the anterior surface 88 and the posterior surface 90 of the entry lens 83 is aspheric as described below. The holder 92 spaces the entry lens 83 from the eye contacting lens 82 so as to collect light rays from the fundus and to produce a real aerial image 94 wherein the image 94 is in close proximity to the entry lens 83. In a preferred embodiment, the optical curvatures of the lenses 82 and 83 and the spacing of the lenses and 82 and 83 form a real aerial image 94 at a position that is less than 40 mm from the posterior surface 84 of the lens 82. In a preferred embodiment, the length, L, of the ophthalmic lens 80 from the anterior surface 88 of the entry lens to the posterior surface 84 of the eye contacting lens is 34 mm or less. Further, the preferred diameter C, of the entry lens 83 is 35 mm or less.

The optical surfaces of the lenses 82 and 83 are defined by the following formula:

$$z = Cr^2/(1+\sqrt{(1-(1+k)c^2 r^2)}) + a1r^2 + a2r^4 + \ldots$$

For the posterior surface 84 of the lens 82, the following values are preferred.
 1/C=7.8+/−1.0
 K=0.088+/−0.1
 A1=0.0000743
For the anterior surface 86 of the lens 82, the following values are preferred.
 1/C=−9.0+/−1.0
 K=−0.4
For an ophthalmic lens 80 having a 1.0× magnification, the following values for the posterior surface 90 of the entry lens are preferred
 1/C=11.5+/−1.0
 K=1.5+/−0.5
and the following values for the anterior surface 88 of the entry lens are preferred.
 1/C=25.8+/−1.0
 K=2.0+/−0.5
For an ophthalmic lens 80 having a 0.7× magnification, the following values for the posterior surface 90 of the entry lens are preferred
 1/C=8.0+/−1.0
 K=−1.7+/−0.5
and the following values for the anterior surface 88 of the entry lens are preferred.
 1/C=−14.0+/−1.0
 K=−2.0+/−0.5

The ophthalmic lenses of the present invention are shaped to optimize the molding process of the lenses and improve the optical quality of the lenses. In particular, the clear aperture of each of the lenses is larger than prior known lenses of the same type. Moreover, because the ophthalmic lenses of the present invention are molded as opposed to machined, the ophthalmic lenses of the present invention can be mass produced in volume at low cost. As such, the ophthalmic lenses of the present invention are particularly suitable for single use applications of the lenses. Because the ophthalmic lenses of the present invention are single use ophthalmic lenses that may be used once and then disposed of, disease transmission via the lenses is substantially minimized.

Many modifications and variations of the present invention are possible in light of the above teachings. Thus, it is to be understood that, within the scope of the appended claims, the invention may be practiced otherwise than as described hereinabove.

What is claimed and desired to be secured by Letters Patent:

1. An ophthalmic lens comprising: a grip portion to be gripped directly or indirectly by a clinician to hold the ophthalmic lens in contact with a patient's eye when the ophthalmic lens is in use, an eye contacting portion and a main body portion disposed between the grip portion and the eye contacting portion wherein the grip portion, the eye contacting portion and the main body portion are integrally formed of an polymethylmethacrylate having a specific gravity of 1.1-1.8, the eye contacting portion is shaped to contact the cornea of the eye, and the main body portion has a curved sidewall with an arc extending in a direction from the grip portion towards the eye contacting portion, the arc having a length that is at least 1.15 times the length of a chord of the arc and the main body portion having at least one mirror surface for reflecting light to and from the eye contacting portion.

2. An ophthalmic lens as recited in claim 1 wherein the specific gravity is 1.15-1.19.

3. An ophthalmic lens as recited in claim 1 further including an aluminum coating on the mirror surface.

4. An ophthalmic lens as recited in claim 1 wherein the acrylic resin is injection molded and/or compression molded.

5. An ophthalmic lens as recited in claim 1 wherein an axis of rotation of the curved sidewall does not coincide with the centerline of the lens.

6. An ophthalmic lens as recited in claim 1 wherein the arc extends from the grip portion to the eye contacting portion.

7. An ophthalmic lens as recited in claim 1 having an index of refraction between 1.2 and 2.0.

8. An ophthalmic lens as recited in claim 1 having a Gonio mirror with a width that is at least 12 mm; a periphery mirror with a width that is at least 15.6 mm and an Arcades mirror with a width that is at least 20 mm.

9. An ophthalmic lens as recited in claim 8 having a length that is at least 27.5 mm.

10. An ophthalmic lens as recited in claim 1 having a Gonio mirror with a width that is at least 12.8 mm; a periphery mirror with a width that is at least 16.6 mm and an Arcades mirror having a width that is at least 21.4 mm.

11. An ophthalmic lens as recited in claim 1 wherein the lens is a Gonio lens having four mirrors each having a width that is at least 15.5 mm.

12. An ophthalmic lens as recited in claim 11 having a length of at least 17 mm.

13. An ophthalmic lens as recited in claim 1 wherein the lens is a Gonio lens having four mirrors each having a width that is at least 15.9 mm.

14. An ophthalmic lens as recited in claim 1 having a single mirror with a width that is at least 13.5 mm.

15. An ophthalmic lens as recited in claim 14 having a length of at least 21 mm.

16. An ophthalmic lens as recited in claim 1 having a single mirror with a width that is at least 13.7 mm.

17. An ophthalmic lens comprising: a grip portion to be gripped directly or indirectly by a clinician to hold the ophthalmic lens in contact with a patient's eye when the ophthalmic lens is in use, an eye contacting portion, and a main body portion disposed between the grip portion and the eye contacting portion wherein the grip portion, the eye contacting portion and the main body portion are integrally formed of molded polymethylmethacrylate, the eye contacting portion is shaped to contact the cornea of the eye, and the main body portion has a curved sidewall with an arc extending in a direction from the grip portion towards the eye contacting portion, the arc having a length that is at least 1.15 times the length of the chord of the arc.

18. An ophthalmic lens as recited in claim 17 wherein the polymethylmethacrylate has a specific gravity of 1.1-1.8.

19. An ophthalmic lens as recited in claim 17 wherein the polymethylmethacrylate has a specific gravity of 1.15-1.19.

20. An ophthalmic lens as recited in claim 17 wherein an axis of rotation of the curved sidewall does not coincide with the centerline of the lens.

21. An ophthalmic lens as recited in claim 17 wherein the arc extends from the grip portion to the eye contacting portion.

22. An ophthalmic lens as recited in claim 17 having an index of refraction between 1.2 and 2.0.

23. An ophthalmic lens as recited in claim 17 having a Gonio mirror with a width that is at least 12 mm; a periphery mirror with a width that is at least 15.6 mm and an Arcades mirror with a width that is at least 20 mm.

24. An ophthalmic lens as recited in claim 23 having a length that is at least 27.5 mm.

25. An ophthalmic lens as recited in claim 17 having a Gonio mirror with a width that is at least 12.8 mm; a periphery mirror with a width that is at least 16.6 mm and an Arcades mirror with a width that is at least 21.4 mm.

26. An ophthalmic lens as recited in claim 17 wherein the lens is a Gonio lens having four mirrors each having a width that is at least 15.5 mm.

27. An ophthalmic lens as recited in claim 26 having a length of at least 17 mm.

28. An ophthalmic lens as recited in claim 17 wherein the lens is a Gonio lens having four mirrors each having a width that is at least 15.9 mm.

29. An ophthalmic lens as recited in claim 17 having a single mirror with a width that is at least 13.5 mm.

30. An ophthalmic lens as recited in claim 29 having a length of at least 21 mm.

31. An ophthalmic lens as recited in claim 17 having a single mirror with a width that is at least 13.7 mm.

32. An ophthalmic lens comprising: a grip portion to be gripped directly or indirectly by a clinician to hold the ophthalmic lens in contact with a patient's eye when the ophthalmic lens is in use, an eye contacting portion and a main body disposed between the grip portion and the eye contacting portion wherein the grip portion, the eye contacting portion and the main body portion are integrally formed of an polymethylmethacrylate having a specific gravity of 1.1-1.8, the eye contacting portion is shaped to contact the cornea of the eye, and the main body portion has a curved sidewall that is described by a sphere having a centerline that does not coincide with the centerline of the lens and at least one flat surface for a mirror for reflecting light to and from the eye contacting portion.

33. An ophthalmic lens as recited in claim 32 wherein the specific gravity is 1.15-1.19.

34. An ophthalmic lens as recited in claim 32 wherein the polymethylmethacrylate is injection molded.

35. An ophthalmic lens as recited in claim 32 wherein the polymethylmethacrylate is compression molded.

36. An ophthalmic lens as recited in claim 32 wherein the curved sidewall has an arc extending from the grip portion to the eye contacting portion wherein the length of the arc is at least 1.15 times the length of a chord of the arc.

37. An ophthalmic lens as recited in claim 32 having an index of refraction between 1.2 and 2.0.

38. An ophthalmic lens comprising: a grip portion to be gripped directly or indirectly by a clinician to hold the ophthalmic lens in contact with a patient's eye when the ophthalmic lens is in use, an eye contacting portion and a main body portion disposed between the grip portion and the eye contacting portion wherein the grip portion, the eye contacting portion and the main body portion are integrally formed of molded polymethylmethacrylate having a specific gravity of 1.1-1.8, the main body portion including four flat surfaces for four mirrors each flat surface having a width of at least 15.5 mm and the ophthalmic lens having a length that is at least 17 mm.

39. An ophthalmic lens as recited in claim 38 wherein the specific gravity of the lens is 1.15-1.19, the width of each of the flat surfaces for the mirrors has a width that is at least 15.9 mm and the length of the ophthalmic lens is at least 17 mm.

40. An ophthalmic lens comprising: a grip portion to be gripped directly or indirectly by a clinician to hold the ophthalmic lens in contact with a patient's eye when the ophthalmic lens is in use, an eye contacting portion and a main body portion disposed between the grip portion and the eye contacting portion wherein the grip portion, the eye contacting portion and the main body portion are integrally formed of molded polymethylmethacrylate having a specific gravity of 1.1-1.8, the main body portion including three flat surfaces for mirrors of different sizes, a first surface for a mirror having a width that is at least 12 mm, a second surface for a mirror having a width that is at least 15.6 mm and a third surface for a mirror having a width that is at least 20 mm and the ophthalmic lens having a length that is at least 27.5 mm.

41. An ophthalmic lens as recited in claim 40 wherein the specific gravity of the lens is 1.15-1.19, the width of the first mirror is at least 12.8 mm, the width of the second mirror is as least 16.6 mm and the width of the third mirror is at least 21.4 mm and the ophthalmic lens having a length that is at least 27.5 mm.

42. An ophthalmic lens comprising: a grip portion to be gripped directly or indirectly by a clinician to hold the ophthalmic lens in contact with a patient's eye when the ophthalmic lens is in use, an eye contacting portion and a main body portion disposed between the grip portion and the eye contacting portion wherein the grip portion, the eye contacting portion and the main body portion are integrally formed of molded polymethylmethacrylate having a specific gravity of 1.1-1.8, the main body portion including a single flat surface for a mirror having a width that is at least 13.5 mm and the ophthalmic lens having a length of at least 21 mm.

43. An ophthalmic lens as recited in claim 42 wherein the specific gravity of the lens is 1.15-1.19, the width of the mirror is at least 13.7 mm and the ophthalmic lens having a length of at least 21 mm.

44. An ophthalmic lens comprising: an eye contacting portion and a magnifying portion opposite the eye contacting portion, the eye contacting portion and the magnifying portion being integrally formed of molded polymethylmethacrylate having a specific gravity of 1.1-1.8, the ophthalmic lens having a clear aperture of at least 11.5 mm and a length of at least 9 mm.

45. An ophthalmic lens as recited in claim 44 wherein the specific gravity of the lens is 1.15-1.19, the clear aperture of the lens is at least 12.5 mm and the length of the lens is at least 11.7 mm.

46. An ophthalmic lens as recited in claim 45 wherein the lens is a capsulotomy lens.

47. An ophthalmic lens as recited in claim 44 wherein the specific gravity of the lens is 1.15-1.19, the clear aperture of the lens is at least 12.5 mm and the length of the lens is at least 10 mm.

48. An ophthalmic lens as recited in claim 47 wherein the lens is an iridotomy lens.

49. An ophthalmic lens as recited in claim 44 wherein the lens is injection and/or compression molded.

50. An ophthalmic lens comprising:
an eye contacting lens formed of molded polymethylmethacrylate having a specific gravity of 1.1-1.8 and an index of refraction of 1.2-2.0; an anterior surface of the eye contacting lens being aspheric;
an entry lens formed of molded polymethylmethacrylate having a specific gravity of 1.1-1.8 and an index of refraction of approximately 1.2-2.0, a posterior surface and an anterior surface of the entry lens being aspheric; wherein the diameter of the entry lens is 35 mm or less; and a holder for spacing the eye contacting lens from the entry lens wherein the length of the ophthalmic lens from a posterior surface of the eye contacting lens to the anterior surface of the entry lens is 34 mm or less.

51. An ophthalmic lens as recited in claim 50 wherein the eye contacting lens and the entry lens have a specific gravity of 1.15-1.19.

52. An ophthalmic lens as recited in claim 50 wherein the eye contacting lens and the entry lens have an index of refraction of approximately 1.49.

53. An ophthalmic lens as recited in claim 50 forming a real image at a distance from a posterior surface of the eye contacting lens that is 40 mm or less.

54. An ophthalmic lens as recited in claim 50 wherein the optical surfaces of the eye contacting lens and the entry lens are defined by the following formula:

$$z = Cr^2/(1+\sqrt{(1-(1+k)c^2r^2)}) + a1r^2 + a2r^4 + \ldots$$

55. An ophthalmic lens as recited in claim 54 wherein a posterior surface of the eye contacting lens has the following values
   $1/C = 7.8 +/- 1.0$
   $K = 0.088 +/- 0.1$
   $A1 = 0.0000743$
and an anterior surface of the eye contacting lens has the following values
   $1/C = -9.0 +/- 1.0$
   $K = -0.4$.

56. An ophthalmic lens as recited in claim 54 wherein a posterior surface of the entry lens has the following values
   $1/C = 11.5 +/- 1.0$
   $K = 1.5 +/- 0.5$
and an anterior surface of the entry lens has the following values
   $1/C = 25.8 +/- 1.0$
   $K = 2.0 +/- 0.5$.

57. An ophthalmic lens as recited in claim 54 wherein a posterior surface of the entry lens has the following values
   $1/C = 8.0 +/- 1.0$
   $K = -1.7 +/- 0.5$
and an anterior surface of the entry lens has the following values
   $1/C = -14.0 +/- 1.0$
   $K = -2.0 +/- 0.5$.

* * * * *